US012595336B2

(12) United States Patent
Ozone et al.

(10) Patent No.: US 12,595,336 B2
(45) Date of Patent: Apr. 7, 2026

(54) METHOD FOR PRODUCING MALEIMIDE POLYETHYLENE GLYCOL DERIVATIVE

(71) Applicant: NOF CORPORATION, Tokyo (JP)

(72) Inventors: Daiki Ozone, Taketoyo-cyo (JP); Shota Mori, Ebina (JP); Masaki Ota, Taketoyo-cyo (JP)

(73) Assignee: NOF CORPORATION, Tokyo (JP)

( * ) Notice: Subject to any disclaimer, the term of this patent is extended or adjusted under 35 U.S.C. 154(b) by 514 days.

(21) Appl. No.: 18/256,951

(22) PCT Filed: Dec. 8, 2021

(86) PCT No.: PCT/JP2021/045098
§ 371 (c)(1),
(2) Date: Jun. 12, 2023

(87) PCT Pub. No.: WO2022/131098
PCT Pub. Date: Jun. 23, 2022

(65) Prior Publication Data

US 2024/0043613 A1 Feb. 8, 2024

(30) Foreign Application Priority Data

Dec. 15, 2020 (JP) ................................. 2020-207847

(51) Int. Cl.
*C08G 65/333* (2006.01)
*A61K 47/60* (2017.01)

(52) U.S. Cl.
CPC ........ *C08G 65/33337* (2013.01); *A61K 47/60* (2017.08)

(58) Field of Classification Search
CPC .............. A61K 47/60; C08G 65/33337; C08G 65/33331
See application file for complete search history.

(56) References Cited

U.S. PATENT DOCUMENTS

| | | | | |
|---|---|---|---|---|
| 7,790,835 | B2 | 9/2010 | Mcmanus et al. | |
| 2005/0176922 | A1* | 8/2005 | McManus ........ | C08G 65/33337 528/310 |
| 2011/0245509 | A1 | 10/2011 | Nakamoto et al. | |
| 2012/0322955 | A1 | 12/2012 | Yoshioka et al. | |
| 2021/0189063 | A1* | 6/2021 | Kinbara ............... | C07D 207/46 |

FOREIGN PATENT DOCUMENTS

| | | | |
|---|---|---|---|
| JP | 61-122241 | A | 6/1986 |
| JP | 2000-191639 | A | 7/2000 |
| JP | 101445477 | A | 6/2009 |
| JP | 2011-225860 | A | 11/2011 |
| WO | WO 2005/056636 | A2 | 6/2005 |
| WO | WO 2012/133490 | A1 | 10/2012 |

OTHER PUBLICATIONS

Combined Chinese Office Action and Search Report issued Jul. 26, 2025 in Chinese Patent Application No. 202180082299.8, 13 pgs.
Chemical Production Technology in the Chemical Engineering Planning Textbooks for Higher Vocational Colleges, edited by Wang Wenjing et al., published by Ocean University Press, pp. 82-64.
International Search Report issued Feb. 22, 2022 in PCT/JP2021/045098 filed on Dec. 8, 2021 2 pages.
Warnecke, A. et al. "Maleimide-oligo (ethylene glycol) Derivatives of Camptothecin as Albumin-Binding Prodrugs: Synthesis and Antitumor Efficacy" Bioconjugate Chem. 2003, 14, 377-387 (11 pages).

* cited by examiner

*Primary Examiner* — Christopher M Rodd
(74) *Attorney, Agent, or Firm* — Oblon, McClelland, Maier & Neustadt, L.L.P.

(57) ABSTRACT

A method for producing a maleimide polyethylene glycol derivative, may including a reaction step of heating a maleimide polyethylene glycol derivative having a protective group, in a solvent in the presence of silica gel to cause deprotection. A maleimide polyethylene glycol derivative can be produced at a high maleimidization rate while restraining deterioration of a maleimide group on deprotecting the maleimide polyethylene glycol derivative having a protective group.

6 Claims, No Drawings

METHOD FOR PRODUCING MALEIMIDE POLYETHYLENE GLYCOL DERIVATIVE

CROSS-REFERENCE TO RELATED APPLICATIONS

The present application is the national stage of international application PCT/JP2021/045098, filed on Dec. 8, 2021, and claims the benefit of the filing date of Japanese Appl. No. 2020-207847, filed on Dec. 15, 2020.

TECHNICAL FIELD

The present invention relates to a method for producing a maleimide polyethylene glycol derivative, which includes subjecting a maleimide polyethylene glycol derivative having a protective group to deprotection of the protective group.

BACKGROUND ART

A drug may be one instable in blood, one which rapidly excretes from the body, one which exhibits antigenicity, or the like. Modification to such a drug with a water-soluble polymer, such as polyethylene glycol (PEG), leads to an improvement in blood retention, and therefore, research on the PEG is actively carried out in the fields of a drug delivery system and medicine. With the PEG modification being done, stabilization of a drug or the like, lowering of antigenicity, reduction of the dose, or the like can be expected, and with an antibody etc. being further bound thereto, the targeting property can be enhanced.

For modifying a biologically active substance, such as a drug, with PEG, it is necessary to convert a terminal group of the PEG into a reactive functional group. In the case where the conversion into the reactive functional group is not sufficient, an unmodified drug or a PEG not converted into a functional group remains as impurities, and therefore, it is necessary to produce a PEG derivative in a high purity.

As one of a reactive functional group, a maleimide group is exemplified. The maleimide group reacts with a thiol group to form a stable thioether, so the maleimide group is well-known as a reactive functional group for a reagent for adding PEG, and is highly useful.

However, the double bond moiety of the maleimide group is highly reactive, and therefore is liable to deteriorate. In the case where a maleimide polyethylene glycol derivative is synthesized through many steps after introduction of the maleimide group, there is a possibility that the introduction rate of the maleimide group (maleimidization rate) is lowered. Therefore, the method of introducing the maleimide group directly at the final step of the synthesis is preferred in view of restraining the deterioration.

With respect to the method, NPL 1 describing the reaction between a PEG derivative and maleimide is exemplified, and according to the described production method, in the case where the hydroxy group at the PEG terminal of the PEG derivative is allowed to react with maleimide at −78° C. in the presence of triphenylphosphine and diisopropyl diazodicarboxylate, the yield rate of the maleimide polyethylene glycol derivative is 31%, and any reason for the low yield rate is not referred.

Furthermore, the reaction between a maleimide derivative, which is synthesized from a furan derivative and maleimide, and a PEG derivative is also reported (PTL 1). In the described production method, the leaving group of the PEG terminal is replaced by a maleimide derivative, and then deprotection by heating is performed to obtain a maleimide PEG derivative. With respect to this method, it is described as an advantage that the use of a maleimide derivative having a protective group which protects the high active double bond of the maleimide at the time of introducing the maleimide group can restrain lowering of the maleimidization rate, while the maleimidization rate is not described. However, it is difficult to prevent the maleimidization rate from lowering at the deprotection process.

CITATION LIST

Patent Literature

PTL 1: US7,790,835B

Non Patent Literature

NPL 1: Bioconjugate Chem., vol. 14, No. 2, 377-387 (2003)

SUMMARY OF INVENTION

Technical Problem

An object of the present invention is to produce a maleimide polyethylene glycol derivative having a high maleimidization rate while restraining deterioration of a maleimide group in subjecting a maleimide polyethylene glycol derivative having a protective group to deprotection.

Solution to Problem

As a result of assiduous researches, the present inventors have found that, by adding silica gel in a reaction system at the time of deprotection, a maleimide polyethylene glycol derivative can be obtained while restraining the deterioration of a maleimide group as compared with the conventional method, thereby completing the present invention.

Namely the present invention relates to the following [1] to [6].

[1] A method for producing a maleimide polyethylene glycol derivative represented by the following general formula (2), including a reaction step of heating a maleimide polyethylene glycol derivative having a protective group represented by the following general formula (1), in a solvent in the presence of silica gel to cause deprotection:

(1)

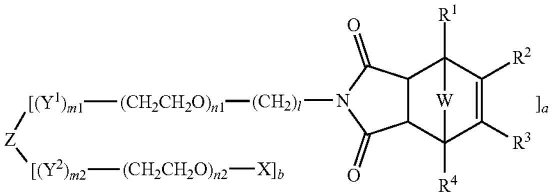

(2)

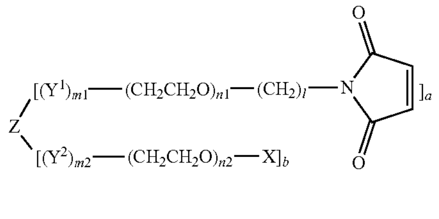

wherein $R^1$, $R^2$, $R^3$, and $R^4$ each independently represents a group selected from a hydrogen atom, an alkyl group, a halogen atom, a cyano group, a formyl group, an acyl group, a carboxy group, an acyloxy group, and an alkylcarbonyloxymethyl group, Z is a residue obtained by removing active hydrogen groups from a compound having 2 to 5 active hydrogen groups, $Y^1$ and $Y^2$ each independently represents a single bond, an ether bond, an amide bond, an ester bond, a urethane bond, a carbonate bond, a thioether bond, a disulfide bond, a thioester bond, or an alkylene group containing any of them, W is a group selected from an ether group, a methylene group and a dimethylvinylidene group, X is a hydrocarbon group having 1 to 7 carbon atoms, a protective group for a hydroxy group, a protective group for a carboxy group, a protective group for a thiol, a cyano group, or an alkylene group containing any of them, m1 and m2 each independently is 1 or 0, n1 represents the number of repeating units of the polyethylene glycol and is an integer of 0 or 10 to 2000, n2 represents the number of repeating units of the polyethylene glycol and is an integer of 10 to 2000, l represents the number of repeating units of the methylene group and is an integer of 0 or 2 to 10, a is an integer of 1 to 5, b is an integer of 0 to 4, and the sum of a and b is an integer of 2 to 5.

[2] The production method according to the above [1], wherein $R^1$, $R^2$, $R^3$, and $R^4$ in the general formula (1) each independently is a hydrogen atom or an alkyl group.

[3] The production method according to the above [1] or [2], wherein W in the general formula (1) is an ether group.

[4] The production method according to any of the above [1] to [3], wherein, in the general formulae (1) and (2), Z is a residue obtained by removing active hydrogen groups from a compound having 2 active hydrogen groups, m1 and m2 each is 1, n1 and n2 each is an integer of 10 to 2000, l is 2, and a and b each is 1.

[5] The production method according to any of the above [1] to [3], wherein, in the general formulae (1) and (2), Z is a residue obtained by removing active hydrogen groups from a compound having 3 active hydrogen groups, m1 is 0, m2 is 1, n1 is 0, n2 is an integer of 10 to 2000, l is 0, a is 1, and b is 2.

[6] The production method according to any of the above [1] to [3], wherein, in the general formulae (1) and (2), Z is a residue obtained by removing active hydrogen groups from a compound having 4 active hydrogen groups, m1 is 1, n1 is from 10 to 2000, l is 2, a is 4, and b is 0.

Advantageous Effects of Invention

According to the present invention, a method for producing a maleimide polyethylene glycol derivative having a high maleimidization rate can be provided.

DESCRIPTION OF EMBODIMENTS

The embodiments of the present invention are described in detail below.

A method for producing a maleimide polyethylene glycol derivative according to the present invention is a method for producing a maleimide polyethylene glycol derivative represented by the following general formula (2), which includes a reaction step of heating a maleimide polyethylene glycol derivative having a protective group represented by the following general formula (1), in a solvent in the presence of silica gel to cause deprotection.

Incidentally the above-described maleimide polyethylene glycol derivative having a protective group is sometimes referred to as "maleimide PEG derivative having a protective group" or "Compound 1". The above-described maleimide polyethylene glycol derivative is sometimes referred to as "maleimide PEG derivative".

(1)

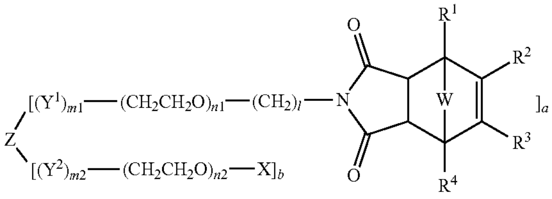

(2)

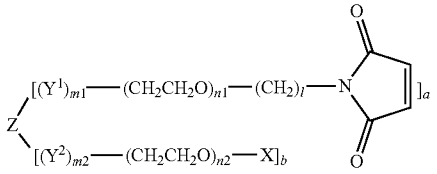

In the formulae, $R^1$, $R^2$, $R^3$, and $R^4$ each independently represents a group selected from a hydrogen atom, an alkyl group, a halogen atom, a cyano group, a formyl group, an acyl group, a carboxy group, an acyloxy group, and an alkylcarbonyloxymethyl group, Z is a residue obtained by removing active hydrogen groups from a compound having 2 to 5 active hydrogen groups, $Y^1$ and $Y^2$ each independently represents a single bond, an ether bond, an amide bond, an ester bond, a urethane bond, a carbonate bond, a thioether bond, a disulfide bond, a thioester bond, or an alkylene group containing them, W is a group selected from an ether group, a methylene group and a dimethylvinylidene group, X is a hydrocarbon group having 1 to 7 carbon atoms, a protective group for a hydroxy group, a protective group for a carboxy group, a protective group for a thiol, a cyano group, or an alkylene group containing them, m1 and m2 each independently is 1 or 0, n1 represents the number of repeating units of the polyethylene glycol and is an integer of 0 or 10 to 2000, n2 represents the number of repeating units of the polyethylene glycol and is an integer of 10 to 2000, l represents the number of repeating units of the methylene group and is an integer of 0 or 2 to 10, a is an integer of 1 to 5, b is an integer of 0 to 4, and the sum of a and b is an integer of 2 to 5.

[Maleimide Polyethylene Glycol Derivative Having a Protective Group Represented by the General Formula (1)]

In the production method of the present invention, a maleimide polyethylene glycol derivative having a protective group represented by the general formula (1) is used as a raw material.

(1)

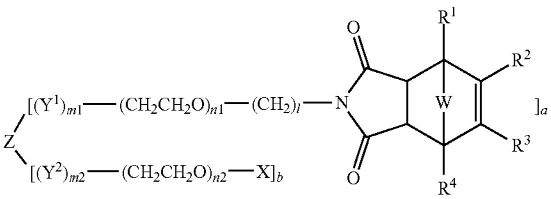

$R^1$, $R^2$, $R^3$, and $R^4$ in formula (1) each independently represents a group selected from a hydrogen atom, an alkyl group, a halogen atom, a cyano group, a formyl group, an acyl group, a carboxy group, an acyloxy group, and an alkylcarbonyloxymethyl group.

Among them, it is preferred that $R^1$, $R^2$, $R^3$, and $R^4$ each independently represents a hydrogen atom or an alkyl group having 1 to 5 carbon atoms, Particularly preferred is the embodiment where $R^1$, $R^2$, $R^3$, and $R^4$ each is a hydrogen atom, the embodiment where $R^2$, $R^3$, and $R^4$ each is a hydrogen atom and $R^1$ is a methyl group, the embodiment where $R^1$, $R^2$, and $R^3$ each is a hydrogen atom and $R^4$ is a methyl group, or the embodiment where $R^2$ and $R^3$ each is a hydrogen atom and $R^1$ and $R^4$ each is a methyl group.

m1 and m2 in the formula (1) each independently is 1 or 0.

n1 in the formula (1) represents the number of repeating units of the polyethylene glycol and is an integer of 0 or 10 to 2000. n1 is preferably an integer of 50 to 1500, more preferably an integer of 100 to 500.

n2 in the formula (1) represents the number of repeating units of the polyethylene glycol and is an integer of 10 to 2000. n2 is preferably an integer of 50 to 1500, more preferably an integer of 100 to 500.

l in the formula (1) represents the number of repeating units of the methylene group and is an integer of 0 or 2 to 10.

a in the formula (1) is an integer of 1 to 5, b is an integer of 0 to 4, and the sum of a and b is an integer of 2 to 5.

Z in the formula (1) is a residue obtained by removing active hydrogen groups from a compound having 2 to 5 active hydrogen groups.

As the active hydrogen group, for example, a hydroxy group, a carboxy group, an amino group, and a thiol group are described, and among them, a hydroxy group is preferred.

As the compound having 2 to 5 of active hydrogen groups, for example, a compound having 1 to 20 carbon atoms, preferably 2 to 10 carbon atoms is described, and examples of the compound include a polyol compound, a polycarbonic acid compound, a polyamine compound, and a polythiol compound, and among them, a polyol compound is preferred.

Examples of the polyol compound include ethylene glycol, propylene glycol, diethylene glycol, triethylene glycol, dipropylene glycol, glycerin, trimethylolpropane, 1,3,6-hexanetriol, pentaerythritol, and sorbitol, and among them, ethylene glycol, glycerin and pentaerythritol are preferred.

With respect to the residue obtained by removing active hydrogen groups from a compound having 2 to 5 active hydrogen groups, if the active hydrogen group is a hydroxy group, the residue means one obtained by removing the hydroxy groups. The illustration is conducted with the following examples. If the compound having 2 to 5 of active hydrogen groups is ethylene glycol, the group represented by the following formula (a1) corresponds to the residue obtained by removing active hydrogen groups from a compound having 2 to 5 active hydrogen groups in the invention. If the compound having 2 to 5 of active hydrogen groups is glycerin, the group represented by the following formula (a2) corresponds to the residue obtained by removing active hydrogen groups from a compound having 2 to 5 active hydrogen groups in the invention. If the compound having 2 to 5 of active hydrogen groups is pentaerythritol, the group represented by the following formula (a3) corresponds to the residue obtained by removing active hydrogen groups from a compound having 2 to 5 active hydrogen groups in the invention. Noted that * in the formula (a1), (a2) or (a3) represents an atomic bonding.

(a1)

$$*-CH_2-CH_2-*$$

(a2)

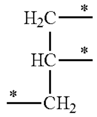

(a3)

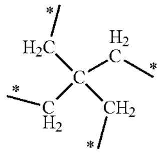

W in the formula (1) is a group selected from an ether group, a methylene group and a dimethylvinylidene group. Among them, W is preferably an ether group (i.e., an oxygen atom) in terms of easiness of protection for the maleimide and deprotection.

$Y^1$ and $Y^2$ in the formula (1) each independently represents a single bond, an ether bond, an amide bond, an ester bond, a urethane bond, a carbonate bond, a thioether bond, a disulfide bond, a thioester bond, or an alkylene group containing any of them.

Among those described above, $Y^1$ and $Y^2$ is preferably an ether group (i.e., an oxygen atom) from the viewpoint of easiness of production.

X in the formula (1) is a hydrocarbon group having 1 to 7 carbon atoms, a protective group for a hydroxy group, a protective group for a carboxy group, a protective group for a thiol, a cyano group, or an alkylene group containing any of them.

As the protective group for a hydroxy group, the protective group for a carboxy group, and the protective group for a thiol, for example, a t-butyl group, a benzyl group, a trityl group, a t-butyldimethylsilyl group, and a t-butyldiphenylsilyl group may be exemplified.

Among them, X is preferably a hydrocarbon group having 1 to 7 carbon atoms, more preferably a methyl group.

With respect to the general formula (1) and the general formula (2) described later, any one of the following embodiments (i) to (iii) is preferred.

(i) Z is a residue obtained by removing active hydrogen groups from a compound having 2 active hydrogen groups, m1 and m2 each is 1, n1 and n2 each is an integer of 10 to 2000, l is 2, and a and b each is 1.

(ii) Z is a residue obtained by removing active hydrogen groups from a compound having 3 active hydrogen groups, m1 is 0, m2 is 1, n1 is 0, n2 is an integer of 10 to 2000, l is 0, a is 1, and b is 2.

(iii) Z is a residue obtained by removing active hydrogen groups from a compound having 4 active hydrogen groups, m1 is 1, n1 is from 10 to 2000, l is 2, a is 4, and b is 0.

The method for producing a maleimide polyethylene glycol derivative having a protective group represented by the general formula (1) is not limited particularly and the maleimide polyethylene glycol derivative having a protective group can be obtained, for example, by preparing the following maleimide protective body (formula (3)) and PEG derivative (formula (4)), and allowing them to react. With respect to the maleimide protective body and the PEG derivative, $R^1$, $R^2$, $R^3$, $R^4$, W, Z, $Y^1$, $Y^2$, X, m1, m2, n1, n2, l, a, and b are the same as in the general formula (1).

(3)

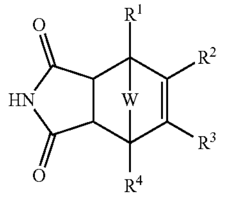

(4)

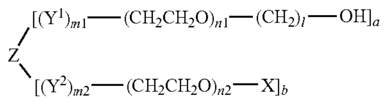

[Method for Producing a Maleimide Polyethylene Glycol Derivative Represented by the General Formula (2)]

The method for producing a maleimide polyethylene glycol derivative represented by the following general formula (2) is a production method including a reaction step of heating a maleimide polyethylene glycol derivative having a protective group represented by the above-described general formula (1), which is in a solvent, in the presence of silica gel to cause deprotection.

(2)

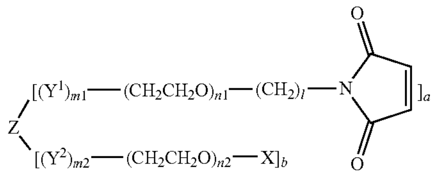

Z, $Y^1$, $Y^2$, X, m1, m2, n1, n2, l, a and b in the formula (2) are the same as in the general formula (1) described above.

The silica gel to be used in the production method of the present invention is a spherical or crushed silicon dioxide.

The average particle size of the silica gel is not limited particularly, and is preferably from 5 to 425 μm, more preferably from 50 to 150 μm.

The average pore size of the silica gel is not limited particularly, and is preferably from 2 to 15 nm, more preferably from 6 to 13 nm.

The average pore volume of the silica gel is not limited particularly and is preferably from 0.5 to 1.5 mL/g, more preferably from 0.6 to 1.2 mL/g.

The specific surface area of the silica gel is not limited particularly and is preferably from 200 to 800 $m^2/g$, more preferably from 250 to 550 $m^2/g$.

When the average particle size, the average pore size, the pore volume and the specific surface area are not less than the respective lower limits of the above-described numeral ranges, the reaction efficiency is enhanced, and when they are not more than the respective upper limits of the above-described numeral ranges, the amount of the aimed product extracted from the residue obtained by filtering out the silica gel is increased to improve the productivity.

The average particle size of the silica gel is a value measured according to a laser diffraction particle size distribution measuring method. The average pore size, the average pore volume and the specific surface area of the silica gel are those measured according to a nitrogen gas adsorption method. Incidentally the specific surface area is the value calculated according to BET isotherm expression.

The amount to be used of the silica gel is preferably from 0.1 to 5 times by weight, particularly preferably from 1 to 3 times by weight with respect to the maleimide PEG derivative having a protective group represented by the general formula (1) (Compound 1). When the used amount of the silica gel is not lower than these lower limits, it is easy to restrain deterioration of the maleimide group, and when the used amount of the silica gel is not more than the upper limits, it is easy to stir the reaction liquid.

The reaction to perform the deprotection according to the present invention is carried out in a solvent by heating. The temperature of the solvent at heating in the present invention (i.e., the reaction temperature) is preferably from 70 to 150° C., above all, particularly preferably from 100 to 120° C. When the temperature of the solvent is not less than the lower limit, the reaction easily proceeds, and when the temperature of the solvent is not more than the upper limit, the deterioration of the maleimide group is easily restrained.

The solvent to be used in the present invention is aprotic and is not limited particularly as long as the solvent has a boiling temperature which is not less than a temperature comparable to the reaction temperature, and is preferably toluene or p-xylene. The amount of the solvent to be used is preferably from 3 to 50 times by weight, more preferably from 5 to 20 times by weight with respect to the maleimide polyethylene glycol derivative having a protective group represented by the general formula (1) (Compound 1). When the used amount of the solvent is not less than the lower limits, it is easy to stir the reaction liquid, and when the used amount of the solvent is not more than the upper limits, the economic efficiency is enhanced.

The reaction time in the present invention is generally from 2 to 8 hours, while it depends on kinds or amount of the raw materials and solvent used.

EXAMPLES

In the following, the present invention is illustrated more specifically based on the examples. In the examples, the analysis on the maleimidization rate was carried out with NMR.

<$^1$H-NMR Analysis Method>

For the analysis with $^1$H-NMR, JNM-ECP400 and JNM-ECA600, manufactured by JEOL Ltd., were used. The integrated value regarding the values measured with NMR measurement is a theoretical value.

According to the following production examples (1-1) to (1-3), a maleimide polyethylene glycol derivative having a protective group (A) (molecular weight: 5,000) was produced.

(A)

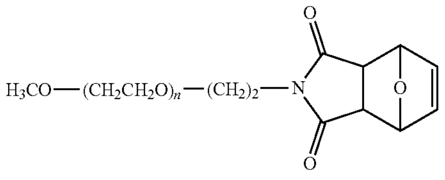

n = 115

Production Example 1-1

Synthesis of Maleimide Protective Body

Into a 9-ml screw tube, 157.1 mg (1.61 mmol) of maleimide, 1.5 g of methyl t-butyl ether, and 876.7 mg (12.88 mmol) of furan were added, and the reaction was performed at 30° C. for 8 hours under a nitrogen atmosphere. Then, the resulting reaction liquid was allowed to cool down to room temperature, and the precipitated crystals were filtered out and dried, thus obtaining the following maleimide protective body (B) (122.9 mg, 0.74 mmol).

(B)

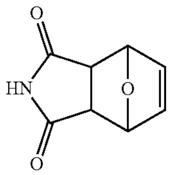

Production Example 1-2

Synthesis of Methoxy PEG (Molecular Weight: 5000)

Into a 200-ml round-bottom flask equipped with a thermometer, a nitrogen-blowing tube, and a stirrer, 24 g (0.8 mol) of dehydrated methanol, and 0.563 g (24 mmol: 16 mol %) of metallic sodium were added, and the resulting mixture was stirred at room temperature while blowing nitrogen thereinto until the metallic sodium dissolved. The resulting solution was charged in a 5 L-autoclave, and the inside of the system was replaced by nitrogen, the temperature was raised to 80° C., 2300 g (52.3 mol) of ethylene oxide was added at 100 to 150° C. and a pressure of 0.5 MPa or less, and the reaction was further performed for one hour. Then, the unreacted ethylene oxide gas was removed under reduced pressure, the temperature was cooled to 60° C., and the pH was adjusted to 7.5 with a 85% aqueous solution of phosphoric acid, thus obtaining the following Compound (C).

$H_3CO—(CH_2CH_2O)_n—(CH_2)_2—OH$ (C)

n=115

Production Example 1-3

Step of Introducing Maleimide Protective Body into Methoxy PEG Derivative

Into a 20 ml-screw tube, 2.00 g (0.40 mmol) of the Compound (C), 3.5 g of dehydrated toluene, 10 g of chloroform, 231.2 mg (1.40 mmol) of the maleimide protective body (B), 1.41 g (5.40 mmol) of triphenyl phosphine, and 1.09 g (5.40 mmol) of diisopropyldiazocarboxylate were charged, and the reaction was performed at room temperature for one hour under a nitrogen atmosphere. After the reaction, 10.0 mg of methanol was added thereto, and the resultant was concentrated at 50° C. The precipitated crystals were dissolved in 10 g of ethyl acetate at 40° C. while heating, and then 8 g of hexane was added thereto to perform crystallization. The precipitated crystals were filtered out, and a mixed solvent of 6 g of hexane and 12 g of ethyl acetate was added to the obtained precipitated crystals. This operation was repeated 4 times, the precipitated crystals were dissolved in 12 g of ethyl acetate at 40° C. while heating, and then 6 g of hexane was added thereto, and crystallization was performed again. Finally, the generated crystals were washed with 8 g of hexane, and dried, thus obtaining the following maleimide polyethylene glycol derivative (A) having a protective group (1.35 g, 0.27 mmol).

(A)

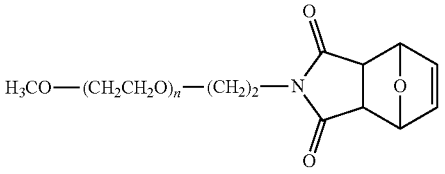

n = 115

A maleimide PEG derivative (D) having a protective group (molecular weight: 20,000) was produced in the same manner as in the above-described Production Examples (1-1) to (1-3) except for changing the charged amount of ethylene oxide in Production Example 1-2 to adjust the molecular weight.

(D)

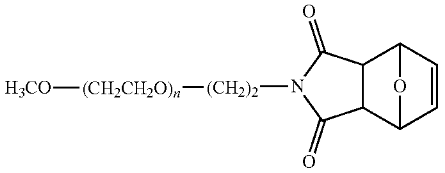

n = 460

According to the following Production Examples (2-1) to (2-7), a maleimide polyethylene glycol derivative (E) having a protective group (molecular weight: 10,000) was produced.

(E)

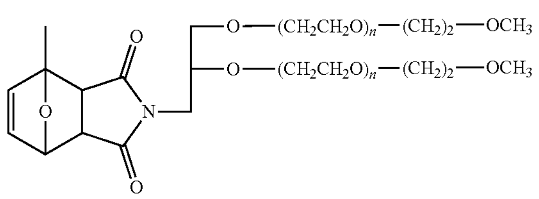

n = 115

Production Example 2-1

Synthesis of Maleimide Protective Body

Into a 9-ml screw tube, 157.1 mg (1.61 mmol) of maleimide, 1.5 g of methyl t-butyl ether, and 877.7 mg (10.68 mmol) of 2-methylfuran were added, and the reaction was performed at 30° C. for 8 hours under a nitrogen atmosphere. Then, the resulting reaction liquid was allowed to cool down to room temperature, and the precipitated crystals were filtered out and dried, thus obtaining the following maleimide protective body (F) (86.4 mg, 0.48 mmol).

(F)

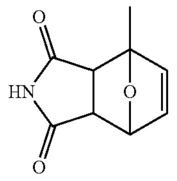

Production Example 2-2

Step of Benzylating Isopropylidene Glycerol

Into a 1000-ml round-bottom flask equipped with a thermometer, a nitrogen-blowing tube, and a stirrer, 132.2 g (1.0 mol) of 2,2-dimethyl-1,3-dioxolane-4-methanol, 231.4 g (1.2 mmol) of a 28% methanol solution of sodium methoxide, and 500 ml of toluene were added, and the toluene was refluxed under reduced pressure for one hour while blowing nitrogen thereinto to distill away the methanol. While the temperature of the resulting solution was maintained at 80° C., 126.6 g (1.0 mol) of benzyl chloride was added dropwise over 2 hours by using a dropping funnel, and for another 2 hours, the reaction was performed. The resulting reaction liquid was desolvated and purified by distillation (b.p. 93 to 95° C./266 Pa) to thereby obtain 4-(benzoxymethyl)-2,2-dimethyl-1,3-dioxolane (G).

(G)

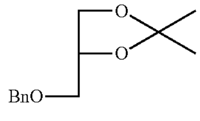

Production Example 2-3

Step of Subjecting Benzyl Protective Isopropylidene Glycerol to Diisopropylidene 222 g (1.0 mol) of the 4-(benzoxymethyl)-2,2-dimethyl-1,3-dioxolane (G), 250 ml of ethanol, and 400 ml of distilled water were measured and put into a 1-L beaker, and the pH of the resulting solution was adjusted to 2.0 with phosphoric acid. The solution was heated up to 70° C. while blowing nitrogen thereinto, the reaction was performed for 1.5 hours, the pH was adjusted to 7.0 with sodium hydroxide, the salts were subjected to adsorption treatment with Kyowaad 1000 (manufactured by Kyowa Chemical Industry Co., Ltd.), and desolvation was performed, thus obtaining 3-benzyloxy-1,2-propanediol (H).

(H)

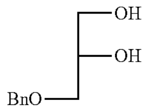

Production Example 2-4

Step of Introducing PEGs into Glycerol Benzyl Protective Body (Molecular Weight: 10,000)

Into a 300-ml round-bottom flask equipped with a thermometer, a nitrogen-blowing tube, and a stirrer, 27.3 g (0.15 mol) of the 3-benzyloxy-1,2-propanediol (H), 127 g (1.2 mol) of dehydrated toluene, and 0.9 g (39 mmol: 26 mol %) of metallic sodium were added, and the resulting solution was stirred at room temperature while blowing nitrogen thereinto until the metallic sodium dissolved. The resulting solution was charged in a 5-L autoclave, the inside of the system was replaced by nitrogen, the temperature was raised to 100° C., 1473 g (33.5 mol) of ethylene oxide was added at 100 to 150° C. and a pressure of 1 MPa or less, and the reaction was further continued for 1 hour. The unreacted ethylene oxide gas was removed at reduced pressure, and the resulting solution was cooled to 60° C., and the pH was adjusted to 7.5 with a 85% aqueous solution of phosphoric acid, thus obtaining the following compound (I).

(I)

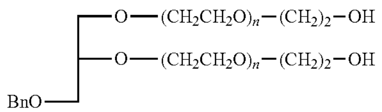

n = 115

Production Example 2-5

Step of Methoxylating Glycerol Benzyl Protective PEG

Into a 500-ml round-bottom flask equipped with a thermometer, a nitrogen-blowing tube, a stirrer, a Dean-Stark tube, and a cooling tube, 100 g (10 mmol) of the above Compound (I) and 320 g of toluene were charged, heat reflux was performed, and the moisture content was removed with azeotropy. The contents were cooled to room temperature, 10.12 g (100 mmol) of triethylamine and 6.87 g (60 mmol) of methanesulfonyl chloride were added thereto, and the reaction was performed at 40° C. for 6 hours. The reaction liquid was filtrated, and the resulting filtrate was transferred into a 500-ml round-bottom flask equipped with a thermometer, a nitrogen-blowing tube, a stirrer, and a cooling tube, and 19.3 g (100 mmol) of a 28% methanol solution of sodium methoxide was added thereto, and the reaction was performed at 70° C. for 6 hours. Subsequently 27 g of Kyowaad 700 (manufactured by Kyowa Chemical Industry Co., ltd.) was added to the reaction liquid, the resulting reaction liquid was further stirred for one hour at 70° C. to subject the excessive sodium methoxide to adsorption treatment, the reaction liquid was filtrated, the filtrate was charged in a 1-L beaker, 300 g of ethyl acetate and 350 g of hexane were added thereto, and crystallization was performed. The precipitated crystals were filtered out into a 1-L beaker, and ethyl acetate was added thereto, the resulting solution was heated at 40° C. such that the crystals dissolved, 300 g of hexane was added thereto, and crystallization was performed again. The precipitated crystals were filtered out and dried, thus obtaining the following Compound (J).

(J)

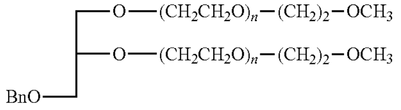

n = 115

Production Example 2-6

Step of Subjecting Glycerol Benzyl Protective PEG to Debenzylation

Into a 500-ml round-bottom flask equipped with a thermometer, a nitrogen-blowing tube, a stirrer, and a cooling tube, 15 g of the above Compound (J) and 15 g of 5% palladium carbon (50% hydrous product) were charged, and after replacement by nitrogen, 300 ml of methanol and 150 ml of cyclohexene were added thereto, the temperature was increased, and the contents were slowly refluxed at 52 to 55° C. to perform the reaction for 5 hours. The resulting reaction liquid was cooled to room temperature, the palladium carbon was filtered out with filtration, and the filtrate was concentrated. To the concentrated liquid, 50 ml of ethyl acetate and 50 ml of hexane were added to perform crystallization. The obtained crystals were filtered out and dried, thus obtaining the following Compound (K).

(K)

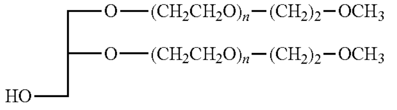

n = 115

Production Example 2-7

Step of Introducing Maleimide Protective Body to Methoxy PEG

Into a 20-ml screw tube, 2.0 g (0.20 mmol) of Compound (K), 3.5 g of dehydrated toluene, 10 g of chloroform, 125.4 mg (0.70 mmol) of the maleimide protective body (F), 708.2 mg (2.70 mmol) of triphenylphosphine, and 546.0 mg (2.70 mmol) of diisopropyldiazodicarboxylate were charged, and the reaction was performed for one hour at room temperature under a nitrogen atmosphere. After the reaction, 10.0 mg of methanol was added thereto, and the resulting reaction liquid was concentrated at 50° C. The precipitated crystals were dissolved in 10 g of ethyl acetate at 40° C. while heating, and 8 g of hexane was added thereto to perform crystallization. The precipitated crystals were filtered out and a mixed solution of 6 g of hexane and 12 g of ethyl acetate were added to the obtained crystals. This operation was repeated 4 times, the precipitated crystals were dissolved in 12 g of ethyl acetate at 40° C. while heating, and then 6 g of hexane was added thereto, and crystallization was performed again. Finally, the generated crystals were washed with 8 g of hexane and dried, thus obtaining the following maleimide polyethylene glycol derivative (E) having a protective group (1.30 g, 0.13 mmol).

(E)

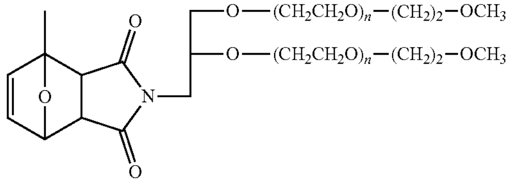

n = 115

According to the following production examples (3-1) to (3-3), a maleimide polyethylene glycol derivative (L) having a protective group (molecular weight: 40,000) was produced.

(L)

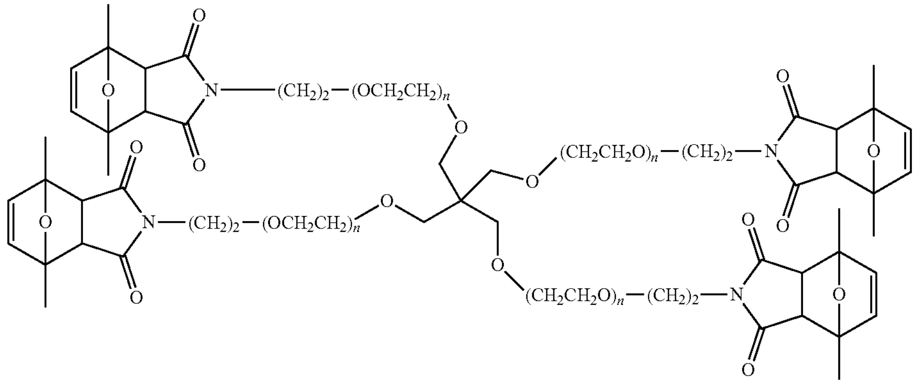

n = 230

Production Example 3-1

Synthesis of Maleimide Protective Body

Into a 9-ml screw tube, 386.9 mg (3.99 mmol) of maleimide, 3.7 g of methyl t-butyl ether, and 3.09 mg (32.14 mmol) of 2,5-dimethylfuran were added, and the reaction was performed for 8 hours at 50° C. under a nitrogen atmosphere. Then, the resulting reaction liquid was allowed to cool down to room temperature, and the precipitated crystals were filtered out and dried, thus obtaining the following maleimide protective body (M) (522.3 mg, 2.70 mmol).

(M)

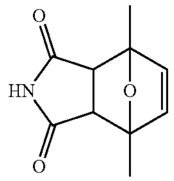

Production Example 3-2

Step of Imparting PEGs to Pentaerythritol

Into a 1000-ml round-bottom flask equipped with a thermometer, a nitrogen-blowing tube, and a stirrer, 24.5 g (0.18 mol) of pentaerythritol, 420 g (4.6 mol) of dehydrated toluene, and 2.5 g (109 mmol: 73 mol %) of metallic sodium were add, and the resulting mixture was stirred at room temperature while blowing nitrogen thereinto until the metallic sodium dissolved. The resulting solution was charged in a 5-L autoclave, the inside of the system was replaced by nitrogen, the temperature was raised to 100° C., 896 g (20.3 mol) of ethylene oxide was added thereto at 100 to 150° C. and a pressure of 1 MPa or less, and then the reaction was further continued for one hour. After unreacted ethylene oxide gas was removed at reduced pressure, the resulting solution was cooled to 60° C., and the pH was adjusted to 7.5 with a 85% aqueous solution of phosphoric acid, thus obtaining the following Compound (N).

(N)

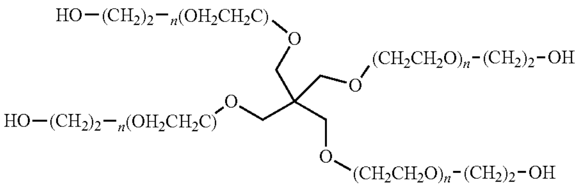

n = 230

Production Example 3-3

Step of Introducing Maleimide Protective Bodies into Pentaerythritol PEG

Into a 20-ml screw tube, 2.0 g (0.050 mmol) of the Compound (N), 3.5 g of dehydrated toluene, 10 g of chloroform, 31.4 mg (0.175 mol) of the maleimide protective body (M), 177.0 mg (0.675 mmol) of triphenylphosphine, and 136.5 mg (0.675 mmol) of diisopropyldiazodicarboxylate were charged, and the reaction was performed for one hour at room temperature under a nitrogen atmosphere. After the reaction, 10.0 mg of methanol was added thereto, and the resulting reaction solution was concentrated at 50° C. The precipitated crystals were dissolved in 10 g of ethyl acetate at 40° C. while heating, and 8 g of hexane was added thereto to perform crystallization. The precipitated crystals were filtered out, and a mixed solvent of 6 g of hexane and 12 g of ethyl acetate was added thereto. This operation was repeated 4 times, the precipitated crystals were dissolved in 12 g of ethyl acetate at 40° C. while heating, and then 8 g of hexane was added thereto, and crystallization was performed again. Finally, the generated crystals were washed with 8 g of hexane and dried, thus obtaining the following maleimide polyethylene glycol derivative (L) having a protective group (1.28 g, 0.032 mmol).

(L)

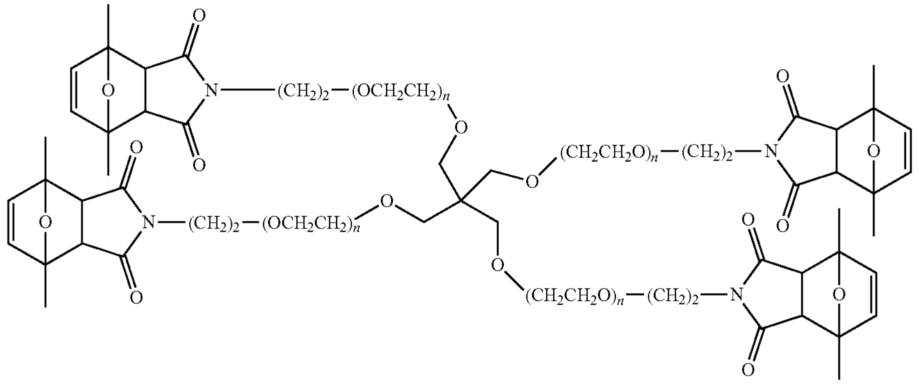

n = 230

Example 1

Method of Producing Maleimide Polyethylene Glycol Derivative

Into a 100-mL side-arm test tube, 200 mg (0.04 mmol) of the maleimide polyethylene glycol derivative (A) having a protective group, 10 g of toluene, and 200 mg of silica gel (PSQ100B, manufactured by Fuji Sylisia Ltd.) were added, and the reaction was performed at 110° C. for 5 hours under a nitrogen atmosphere. The reaction liquid was subjected to decantation, and then, the aimed product was extracted from the silica gel with 4 g of methanol twice. The reaction liquid and the extraction liquid were transferred into a 50-mL egg-plant flask, and concentrated to dryness, followed by vacuum drying for 6 hours, thus obtaining a maleimide polyethylene glycol derivative (O) (yield: 189.5 mg, 0.037 mmol, yield rate: 96%, maleimidization rate: 97%). The silica gel (PSQ100B, manufactured by Fuji Sylisia Ltd.) used in the present example has an average particle size of 100 μm, an average pore size of 7 nm, a pore volume of 0.8 mL/g and a specific surface area of 500 $m^2$/g.

(O)

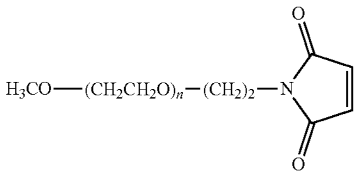

n = 115

In the $^1$H-NMR of the maleimide polyethylene glycol derivative (O) obtained in Example 1, any peaks at 6.51 ppm and 6.42 ppm, which are derived from the maleimide polyethylene glycol derivative (A) having a protective group, were not present, and therefore, it was confirmed that the deprotection was complete. The integrated value of the peak at 6.71 ppm, which is derived from the vinyl proton of the maleimide group, was 1.94, and therefore, it was confirmed that the aimed maleimide polyethylene glycol derivative represented by the formula (2) was obtained at a maleimidization rate of 97%.

Example 2

Method of Producing Maleimide Polyethylene Glycol Derivative

Into a 100-mL side-arm test tube, 200 mg (0.01 mmol) of the maleimide polyethylene glycol derivative (D) having a protective group, 10 g of toluene, and 200 mg of silica gel (PSQ100B, manufactured by Fuji Sylisia Ltd.) were added, and the reaction was performed at 110° C. for 5 hours under a nitrogen atmosphere. The reaction liquid was subjected to decantation, and then, the aimed product was extracted from the silica gel with 4 g of methanol twice. The reaction liquid and the extraction liquid were transferred into a 50-mL egg-plant flask, and concentrated to dryness, followed by vacuum drying for 6 hours, thus obtaining a maleimide polyethylene glycol derivative (P) (yield: 191.4 mg, 0.0095 mmol, yield rate: 96%, maleimidization rate: 97%). The silica gel (PSQ100B, manufactured by Fuji Sylisia Ltd.) used in the present example has an average particle size of 100 μm, an average pore size of 7 nm, a pore volume of 0.8 mL/g and a specific surface area of 500 $m^2$/g.

(P)

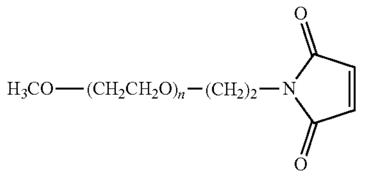

n = 460

In the $^1$H-NMR of the maleimide polyethylene glycol derivative (P) obtained in Example 2, any peaks at 6.51 ppm and 6.42 ppm, which are derived from the maleimide polyethylene glycol derivative (D) having a protective group, were not present, and therefore, it was confirmed that the deprotection was complete. The integrated value of the peak at 6.71 ppm, which is derived from the vinyl proton of the maleimide group, was 1.94, and therefore, it was confirmed that the aimed maleimide polyethylene glycol derivative (P) represented by the formula (2) was obtained at a maleimidization rate of 97%.

Example 3

Method of Producing Maleimide Polyethylene Glycol Derivative

Into a 100-mL side-arm test tube, 200 mg (0.02 mmol) of the maleimide polyethylene glycol derivative (E) having a protective group, 10 g of toluene, and 200 mg of silica gel (PSQ100B, manufactured by Fuji Sylisia Ltd.) were added, and the reaction was performed at 110° C. for 5 hours under a nitrogen atmosphere. The reaction liquid was subjected to decantation, and then, the aimed product was extracted from the silica gel with 4 g of methanol twice. The reaction liquid and the extraction liquid were transferred into a 50-mL egg-plant flask, and concentrated to dryness, followed by vacuum drying for 6 hours, thus obtaining a maleimide polyethylene glycol derivative (Q) (yield: 188.3 mg, 0.019 mmol, yield rate: 95%, maleimidization rate: 96%). The silica gel (PSQ100B, manufactured by Fuji Sylisia Ltd.) used in the present example has an average particle size of 100 μm, an average pore size of 7 nm, a pore volume of 0.8 mL/g and a specific surface area of 500 $m^2$/g.

(Q)

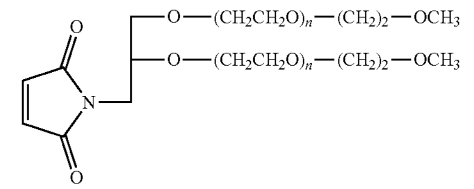

n = 115

In the $^1$H-NMR of the maleimide polyethylene glycol derivative (Q) obtained in Example 3, any peaks at 6.55 ppm, 6.41 ppm, 6.35 ppm, and 6.24 ppm, which are derived from the maleimide polyethylene glycol derivative (E) having a protective group, were not present, and therefore, it was confirmed that the deprotection was complete. The integrated value of the peak at 6.71 ppm, which is derived from the vinyl proton of the maleimide group, was 1.92, and therefore, it was confirmed that the aimed maleimide polyethylene glycol derivative (Q) represented by the formula (2) was obtained at a maleimidization rate of 96%.

Example 4

Method of Producing Maleimide Polyethylene Glycol Derivative

Into a 100-mL side-arm test tube, 200 mg (0.005 mmol) of the maleimide polyethylene glycol derivative (L) having a protective group, 10 g of toluene, and 200 mg of silica gel (PSQ100B, manufactured by Fuji Sylisia Ltd.) were added, and the reaction was performed at 110° C. for 5 hours under a nitrogen atmosphere. The reaction liquid was subjected to decantation, and then, the aimed product was extracted from the silica gel with 4 g of methanol twice. The reaction liquid and the extraction liquid were transferred into a 50-mL egg-plant flask, and concentrated to dryness, followed by vacuum drying for 6 hours, thus obtaining a maleimide polyethylene glycol derivative (R) (yield: 194.0 mg, 0.0048 mmol, yield rate: 98%, maleimidization rate: 96%). The silica gel (PSQ100B, manufactured by Fuji Sylisia Ltd.) used in the present example has an average particle size of 100 μm, an average pore size of 7 nm, a pore volume of 0.8 mL/g and a specific surface area of 500 m2/g.

(R)

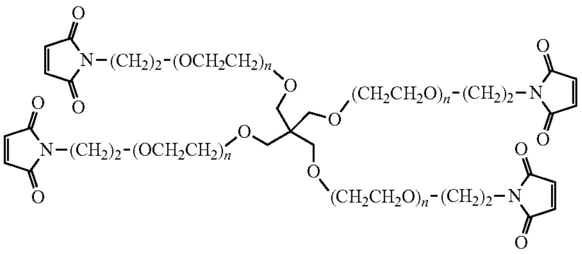

n = 230

In the $^1$H-NMR of the maleimide polyethylene glycol derivative (R) obtained in Example 4, any peaks at 6.35 ppm and 6.23 ppm, which are derived from the maleimide polyethylene glycol derivative (L) having a protective group, were not present, and therefore, it was confirmed that the deprotection was complete. The integrated value of the peak at 6.71 ppm, which is derived from the vinyl proton of the maleimide group, was 1.92, and therefore, it was confirmed that the aimed maleimide PEG derivative (R) represented by the formula (2) was obtained at a maleimidization rate of 96%.

Comparative Example 1

Method of Producing Maleimide Polyethylene Glycol Derivative

Into a 100-mL three-necked round-bottom flask, 200 mg (0.04 mmol) of the maleimide polyethylene glycol derivative (A) having a protective group, and 10 g of toluene were added, and the reaction was performed at 110° C. for 5 hours under a nitrogen atmosphere. The reaction liquid was transferred into a 50-mL egg-plant flask, and concentrated to dryness, followed by vacuum drying for 6 hours, thus obtaining a maleimide polyethylene glycol derivative (O) (yield: 195.4 g, 0.038 mmol, yield rate: 99%, maleimidization rate: 85%).

In the $^1$H-NMR of the maleimide polyethylene glycol derivative (O) obtained in Comparative Example 1, any peaks in a range of 6.51 ppm and 6.42 ppm, which are derived from the maleimide polyethylene glycol derivative (A) having a protective group, were not present, and therefore, it was confirmed that the deprotection was complete. The integrated value of the peak at 6.71 ppm, which is derived from the vinyl proton of the maleimide group, was 1.70, and therefore, it was confirmed that the aimed maleimide PEG derivative (O) represented by the formula (2) was obtained at a maleimidization rate of 85%.

Comparative Example 2

Method of Producing Maleimide Polyethylene Glycol Derivative

Into a 100-mL side-arm test tube, 150 mg (0.0037 mmol) of the maleimide PEG derivative (L) having a protective group, 7.5 g of toluene, and 150 mg of Kyowaad 2000 (a solid solution of aluminum oxide and magnesium oxide, manufactured by Kyowa Chemical Industry Co., ltd.) were added, and the reaction was performed at 110° C. for 5 hours under a nitrogen atmosphere. The reaction liquid was subjected to decantation, and then, the aimed product was extracted with 3 g of methanol twice. The reaction liquid and the extraction liquid were transferred into a 50-mL egg-plant flask, and concentrated to dryness, followed by vacuum drying for 6 hours, thus obtaining a maleimide polyethylene glycol derivative (R) (yield: 87.5 mg, 0.0021 mmol, yield rate: 59%, maleimidization rate: 65%).

In the $^1$H-NMR of the maleimide polyethylene glycol derivative (R) obtained in Comparative Example 2, any peaks in a range of 6.35 μm and 6.23 ppm, which are derived from the maleimide polyethylene glycol derivative (L) having a protective group, were not present, and therefore, it was confirmed that the deprotection was complete. The integrated value of the peak at 6.71 ppm, which is derived from the vinyl proton of the maleimide group, was 1.30, and therefore, it was confirmed that the aimed maleimide polyethylene glycol derivative (R) represented by the formula (2) was obtained at a maleimidization rate of 65%.

As described above, a method of producing a maleimide polyethylene glycol derivative at a high maleimidization rate can be provided by heating a maleimide polyethylene glycol derivative having a protective group in a solvent in the presence of silica gel.

The invention claimed is:

1. A method for producing a maleimide polyethylene glycol derivative represented by the following general formula (2), comprising a reaction step of heating a maleimide polyethylene glycol derivative having a protective group represented by the following general formula (1), in a solvent in the presence of silica gel to cause deprotection:

(1)

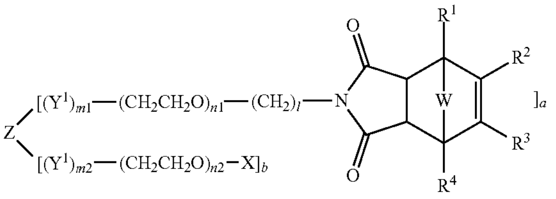

(2)

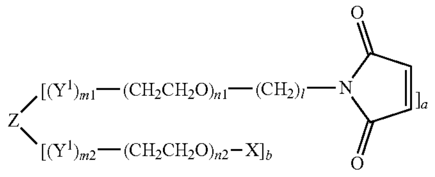

wherein $R^1$, $R^2$, $R^3$, and $R^4$ each independently represents a group selected from a hydrogen atom, an alkyl group, a halogen atom, a cyano group, a formyl group, an acyl group, a carboxy group, an acyloxy group, and an alkylcarbonyloxymethyl group, Z is a residue obtained by removing active hydrogen groups from a compound having 2 to 5 active hydrogen groups, $Y^1$ and $Y^2$ each independently represents a single bond, an ether bond, an amide bond, an ester bond, a urethane bond, a carbonate bond, a thioether bond, a disulfide bond, a thioester bond, or an alkylene group containing any of them, W is a group selected from an ether group, a methylene group and a dimethylvinylidene group, X is a hydrocarbon group having 1 to 7 carbon atoms, a protective group for a hydroxy group, a protective group for a carboxy group, a protective group for a thiol, a cyano group, or an alkylene group containing any of them, m1 and m2 each independently is 1 or 0, n1 represents the number of repeating units of the polyethylene glycol and is an integer of 0 or 10 to 2000, n2 represents the number of repeating units of the polyethylene glycol and is an integer of 10 to 2000, l represents the number of repeating units of the methylene group and is an integer of 0 or 2 to 10, a is an integer of 1 to 5, b is an integer of 0 to 4, and the sum of a and b is an integer of 2 to 5.

2. The method of claim 1, wherein $R^1$, $R^2$, $R^3$, and $R^4$ in the general formula (1) each independently is a hydrogen atom or an alkyl group.

3. The method of claim 1, wherein W in the general formula (1) is an ether group.

4. The method of claim 1, wherein, in the general formulae (1) and (2), Z is a residue obtained by removing active hydrogen groups from a compound having 2 active hydrogen groups, m1 and m2 each is 1, n1 and n2 each is an integer of 10 to 2000, l is 2, and a and b each is 1.

5. The method of claim 1, wherein, in the general formulae (1) and (2), Z is a residue obtained by removing active hydrogen groups from a compound having 3 active hydrogen groups, m1 is 0, m2 is 1, n1 is 0, n2 is an integer of 10 to 2000, l is 0, a is 1, and b is 2.

6. The method of claim 1, wherein, in the general formulae (1) and (2), Z is a residue obtained by removing active hydrogen groups from a compound having 4 active hydrogen groups, m1 is 1, n1 is from 10 to 2000, l is 2, a is 4, and b is 0.

* * * * *